US010247664B2

(12) United States Patent
Ye et al.

(10) Patent No.: US 10,247,664 B2
(45) Date of Patent: Apr. 2, 2019

(54) QUANTIFICATIONAL TESTING METHOD FOR SEMEN LIQUEFACTION ABILITY

(71) Applicant: AHEAD BIOTECH CO., LTD., Huanyuan Hi-Tech Park (CN)

(72) Inventors: Tao Ye, Huanyuan Hi-Tech Park (CN); Jiang Liu, Huanyuan Hi-Tech Park (CN); Yuan Li, Huanyuan Hi-Tech Park (CN); Shan Xue, Huanyuan Hi-Tech Park (CN)

(73) Assignee: AHEAD BIOTECH CO., LTD., Huanyuan Hi-Tech Park (CN)

( * ) Notice: Subject to any disclaimer, the term of this patent is extended or adjusted under 35 U.S.C. 154(b) by 7 days.

(21) Appl. No.: 15/510,433

(22) PCT Filed: Aug. 31, 2015

(86) PCT No.: PCT/CN2015/088571
§ 371 (c)(1),
(2) Date: Mar. 10, 2017

(87) PCT Pub. No.: WO2016/037536
PCT Pub. Date: Mar. 17, 2016

(65) Prior Publication Data
US 2017/0261424 A1 Sep. 14, 2017

(30) Foreign Application Priority Data

Sep. 11, 2014 (CN) .......................... 2014 1 0459737

(51) Int. Cl.
*G06K 9/00* (2006.01)
*G01N 21/27* (2006.01)
(Continued)

(52) U.S. Cl.
CPC ........... *G01N 21/27* (2013.01); *G06T 7/0012* (2013.01); *G06T 7/0016* (2013.01); *G06T 7/90* (2017.01);
(Continued)

(58) Field of Classification Search
CPC .. A61K 36/8962; A61K 36/746; A61K 36/39; A61K 2236/333; A23L 33/30;
(Continued)

(56) References Cited

U.S. PATENT DOCUMENTS 5,744,366 A * 4/1998 Kricka .................. B01D 61/18
422/400
2007/0031895 A1 * 2/2007 Herr .................... A61B 10/0058
435/7.2
(Continued)

FOREIGN PATENT DOCUMENTS

CN 1635378 A 7/2005
CN 101644706 2/2010
(Continued)

OTHER PUBLICATIONS

International Search Report dated Dec. 4, 2015 in corresponding Application No. PCT/CN2015/088571; 4 pgs.
(Continued)

*Primary Examiner* — Amir Alavi
(74) *Attorney, Agent, or Firm* — Maier & Maier, PLLC

(57) ABSTRACT

This invention publicly announces a quantificational testing method of semen liquefaction ability. By following the steps of sample preparation, image collection, image quantificational analysis and curve analysis to analyze the quantificational testing of semen liquefaction ability; indirectly indicate the semen liquefaction ability by observing the color depth change in the sperm sampled cover black area; to analyze the quantification of semen liquefaction by observing the level of change in grey level value versus time; thus, to efficiently, subjectively and standardly test the semen liquefaction ability and avoid human errors.

10 Claims, 6 Drawing Sheets

(51) Int. Cl.
*G06T 7/90* (2017.01)
*G06T 7/00* (2017.01)

(52) U.S. Cl.
CPC ....... *G01N 21/272* (2013.01); *G01N 2201/12* (2013.01); *G06T 2207/10016* (2013.01); *G06T 2207/10024* (2013.01); *G06T 2207/30024* (2013.01)

(58) Field of Classification Search
CPC .......... A23L 33/105; A23L 2/52; A23L 33/10; A23P 10/40; A23P 10/28; A23P 10/30; A23V 2002/00; G01N 21/27; G01N 2201/12; G06T 7/0012; G06T 7/90
See application file for complete search history.

(56) References Cited

U.S. PATENT DOCUMENTS

| | | | | |
|---|---|---|---|---|
| 2014/0141420 | A1* | 5/2014 | Stahl | C12Q 1/6883 435/6.11 |
| 2016/0120930 | A1* | 5/2016 | Giversen | A61K 36/9062 424/756 |
| 2016/0356785 | A1* | 12/2016 | Sergeant | G01N 33/689 |
| 2017/0106040 | A1* | 4/2017 | Park | A61K 36/8962 |
| 2017/0261424 | A1* | 9/2017 | Ye | G01N 21/27 |

FOREIGN PATENT DOCUMENTS

| | | |
|---|---|---|
| CN | 102209891 A | 10/2011 |
| CN | 104251823 A | 12/2014 |
| EP | 2421360 A1 | 2/2012 |
| JP | H08297087 A | 11/1996 |

OTHER PUBLICATIONS

Lu, Meige et al, "Detection of fibrin degradation products in normal and abnormal seminal plasma", Journal of Reproductive Medicine, vol. 2, No. 2, Feb. 28, 1993(Feb. 28, 1993), p. 111, 1 pg.

Li, Yonghai, Abnormal semen liquefaction', Chinese Journal of Andrology, vol. 4, No. 2, Feb. 28, 1994 (Feb. 28, 1994) pp. 113-116, 4 pgs.

Zhang, Jiyun, Research Progress on chemical composition of semen liquefaction, Journal of Shandong Medical College, vol. 32, No. 1, Jan. 31, 2012 (Jan. 31, 2012), pp. 74-77, 4 pgs.

* cited by examiner

QUANTIFICATIONAL TESTING METHOD FOR SEMEN LIQUEFACTION ABILITY

TECHNICAL AREA

This invention involves medical technic area, in detail; it involves semen liquefaction ability testing method.

TECHNICAL BACKGROUND

When the semen is discharged from human body is uneasy to flow and its form is white jelly like; under normal conditions, the semen is changed from flow able white jelly form like to relatively transparent fluid with fluidity; this process is semen liquefaction process. Semen's inability to liquefaction or lower-level liquefaction is one of important reasons for males' infertility. At this stage, the method for semen liquefaction is as flowing; placing the semen sample in the container and letting it sits for a while (normally 60 minutes); then, the lab operator evaluates the semen fluidity to obtain the results; such method processes long waiting time and human error, which is not subjective and standard; such method is unable to analyze the quantification of semen liquefaction ability.

INVENTION CONTENT

To be able to solve the technical problem in above, the goal of this invention is to provide a method for testing the quantification analysis for sperm liquefaction ability.

The achievement of the goal of this invention is as followings:

Step 1: Sample Preparation

Adding semen sample to the testing sample system; installing black sample pool inside the sample's system; adding semen sample to the sample pool.

Step 2: Image Collection

Starting from adding semen sample to sample pool, collecting the sample pool's semen sample Images following the time order to receive analyzing images.

Step 3: Sample Quantification Analysis

Calculating each image's gray level value to gain grey level value versus time graph; the ratio difference of the graph represents the change in color on the image within the timeline.

Step 4: Graph Analysis

Semen liquefaction ability is related to images' changes in color; the graph also represents semen liquefaction ability. The semen liquefaction ability analysis is gained by obtaining gray level change within unit time; more change of gray level value within unit time represents stronger semen liquefaction ability, less change of gray level within unit time represents weaker semen liquefaction ability.

When the semen would appear in color when it is placed in the sample pool in the beginning; semen sample would cover up the black bottom; the collected image would appear in white or whitish at this time; as the semen gradually liquidizes, the color of it changes from white to relatively transparent, and color of black bottom gradually enhances.

The stronger the semen liquefaction ability the less time spent for it to change from white to transparent; the bottom of black color would appear faster; collected images' color depth would change faster.

The weaker the semen liquefaction ability the more time spent for it to change from white to transparent; the bottom of black color would appear slower; collected images' color depth would change slower.

Thus, collecting the images from the sample and sample pool in real time and observing the bottom of the sample pool's black color's appearance speed dynamically. Such method would be able to test the semen liquefaction ability in the sample proof by the level of color depth change indirectly.

The depth of the color can be quantified by the grey level ratio of the color; the change in the depth of the color's grey level value presents the change in color's depth. Thus, trough the relationship in the change between grey level value and time, it could indirectly carry out quantificational analysis for the semen liquefaction ability. And the relationship in change between grey level value and time could be represented by change in ratio of grey level value versus time graph within unit time.

Thus, the higher the change in ratio of grey level values within unit time, the stronger the semen liquefaction ability.

Thus, the lower the change in ratio of grey level values within unit time, the weaker the semen liquefaction ability.

According to step 1 in the above, semen sample is placed at 2-5 mm in the relative sample pool. The thickness of semen sample affects the collector from picking blackness samples from bottom of the pool; if the semen sample is placed too high in sample pool could cause the image collector to slow down and become insensitivity to change in color. If the semen sample is placed too low in the sample pool can cause over sensibility of the image collector towards the change in depth of color. Both are unable to estimate suitable grey level value change graph.

According to step 1 in the above, after semen sample is placed in the sample pool, closing the top of the sample pool with transparent cover. On one hand, transparent cover could isolate the semen sample, avoid outside circumstances affecting semen liquefaction and avoid effects on the image collector's collection on top of the sample pool. On the other hand, when comparing different semen samples' liquefaction abilities; the samples have to be placed at the height in the pool; when using transparent cover to cover up the sample pool, human control is not needed; only by filling up sample in the sample pool and using the transparent cover to squeeze out surplus sample out the sample pool to add semen sample to make sure adding semen sample to pool to maintain even surface at each time form more convenient and easier height control.

According to step 2 in the image collecting process, collecting the semen sample image in the sample pool on top at the same height.

According to step 2 in the image collection process, collecting the semen sample image in the sample pool on top at the same time rate.

The time gap is 5-60 seconds in the image collection process.

According to step 2 in the image collection process, the collection of images is operated under stable light source.

According to the step 3 in the image quantification analysis, picking each appointed analyzing image's same and stable area to form calculation zone; calculating the grey value in the calculating zone to form analyzing images' grey versus time graph.

According to the step 3 in the image quantification analysis, utilizing RBG's color system and 8-digit image calculated grey value; standard pure white grey value is 255.

The actual estimated total grey level value in the appointed calculating area is calculated by using formula 1:

$$\text{Grey Level Value} = \sum_{i=1}^{n} x_i \quad \text{Formula 1}$$

The actual estimated average grey level value of assigned area is calculated by using formula 2.

$$\text{Grey Level Value} = \sum_{i=1}^{n} x_i / n \quad \text{Formula 2}$$

The semen sample's entire grey level value of assigned area is calculated by using formula 3.

$$\text{Grey Level Value} = \sum_{i=1}^{n} (255 - x_i) \quad \text{Formula 3}$$

The semen sample's entire average value of assigned area is calculated by using formula 4.

$$\text{Grey Level Value} = \sum_{i=1}^{n} (255 - x_i) / n \quad \text{Formula 4}$$

In the calculation, n is number of appointed calculating areas' pixel spot; xi is actual estimated grey level in the pointed calculating area's each digital pixel spot.

The testing sample system in the above includes testing card and light source above the testing card; the testing card would have testing pool cover groove placed on top of it; the sample pool is built underneath the testing pool cover groove; the bottom of this sample pool is black; transparent cover board is placed in the testing cover groove; surplus liquid groove is placed in the testing card; the surplus liquid groove is connected to sample pool trough overflow groove; one side of the overflow groove is connected to the top of the sample pool; the image collector is stably placed on the direct top of the sample pool; the image collector is connected to cellphone through wire of wireless connection; the cellphone is connected to long distant computer. By using the sample testing system provided by this design is able to accomplish the followings: collecting the images of the semen sample during the semen liquefaction process in real time; image collector is connected to cellphone trough cable of wireless connection to send to collected images information to cellphone; cellphone would be able to send the compressed images data to long distant computer; long distant computer would then complete the analysis for image data and grey level value's color level value calculation, obtaining testing results and sending back to cell's App at live scene.

Advantages of using method of testing the quantification of the semen liquefaction ability of this invention are as followings: semen liquefaction ability is represented by the color change in the semen sample covered black zone indirectly; analyze the quantification of semen liquefaction ability by the changed level of the grey level versus time; to efficiently, objectively and standardly test semen liquefaction ability, in order to avoid human error in the testing analysis.

DETAILED IMPLEMENTING METHOD

ONE. To further explain this invention by the combination of implementing examples and figures.

Figure 1:
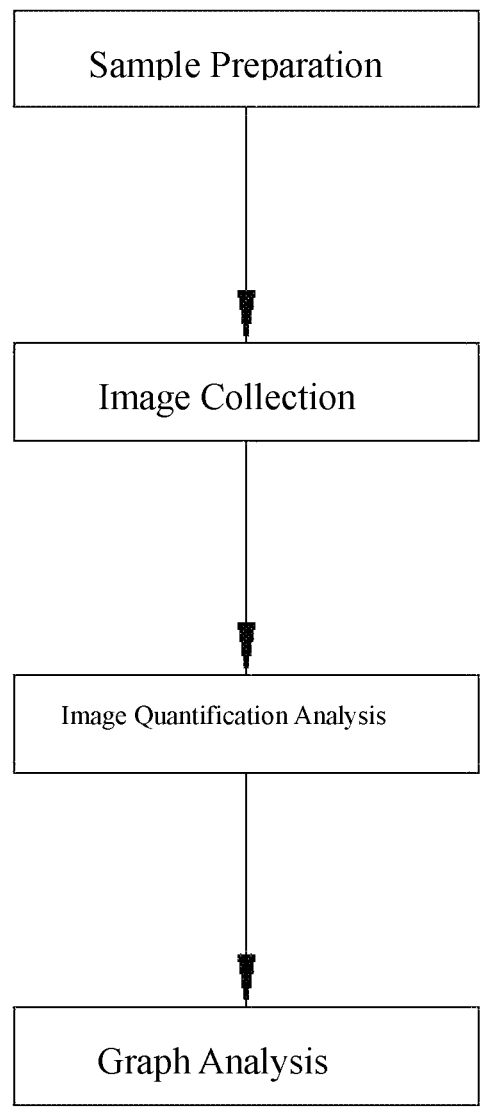
FIG. 1: procedure image of the method of testing quantification of the semen liquefaction ability in this invention.

According to FIG. 1, a method of testing the quantification of semen liquefaction by the following steps:

Step 1: Sample Preparation

Adding semen sample into testing sample system within 2 minutes of semen come out from the penis; placing black bottom sample pool inside the sample system; adding semen sample into the sample pool; semen sample is placed 2-5 millimeters in the sample pool; after placing the semen sample into the sample pool, covering the sample pool with transparent cover.

Step 2: Image Collection

Beginning with semen sample being added to the sample pool, collecting sample pool's semen sample images at the same height above the semen pool at time gap between 5-60 seconds.

When collection the images, the process must undergo under stable natural light source; if the natural sunlight is unstable, the process must undergo under stable artificial light source.

Step 3: Image Quantification Analysis

Choosing the same stable area of each analyzed image to form calculation area; utilizing RBG color system and 8-digit to calculate the area's grey level; the standard pure with grey level is 255 at this time.

The actual estimated total grey level value in the appointed calculating area is calculated by using formula 1:

$$\text{Grey Level Value} = \sum_{i=1}^{n} x_i \quad \text{Formula 1}$$

The actual estimated average grey level value of assigned area is calculated by using formula 2.

$$\text{Grey Level Value} = \sum_{i=1}^{n} x_i / n \quad \text{Formula 2}$$

The semen sample's entire grey level value of assigned area is calculated by using formula 3.

$$\text{Grey Level Value} = \sum_{i=1}^{n} (255 - x_i) \quad \text{Formula 3}$$

The semen sample's entire average value of assigned area is calculated by using formula 4.

$$\text{Grey Level Value} = \sum_{i=1}^{n} (255 - x_i)/n \quad \text{Formula 4}$$

In the calculation, n is number of appointed calculating areas' pixel spot; xi is actual estimated grey level value in the pointed calculating area's each digital pixel spot.

The grey level value versus time graph represents the analyzed image depth change degree within unit time.

Step 4: Graph Analysis

The ability of semen liquefaction is related to change in color depth of analyzing image; the change ratio of grey level value versus time graph represents the semen liquefaction ability; to analyze the quantification of semen liquefaction ability through change ratio of grey level within unit time; higher change ratio of grey level value within unit time presents stronger liquefaction ability, otherwise, weaker sperm liquefaction ability.

Figure 2:
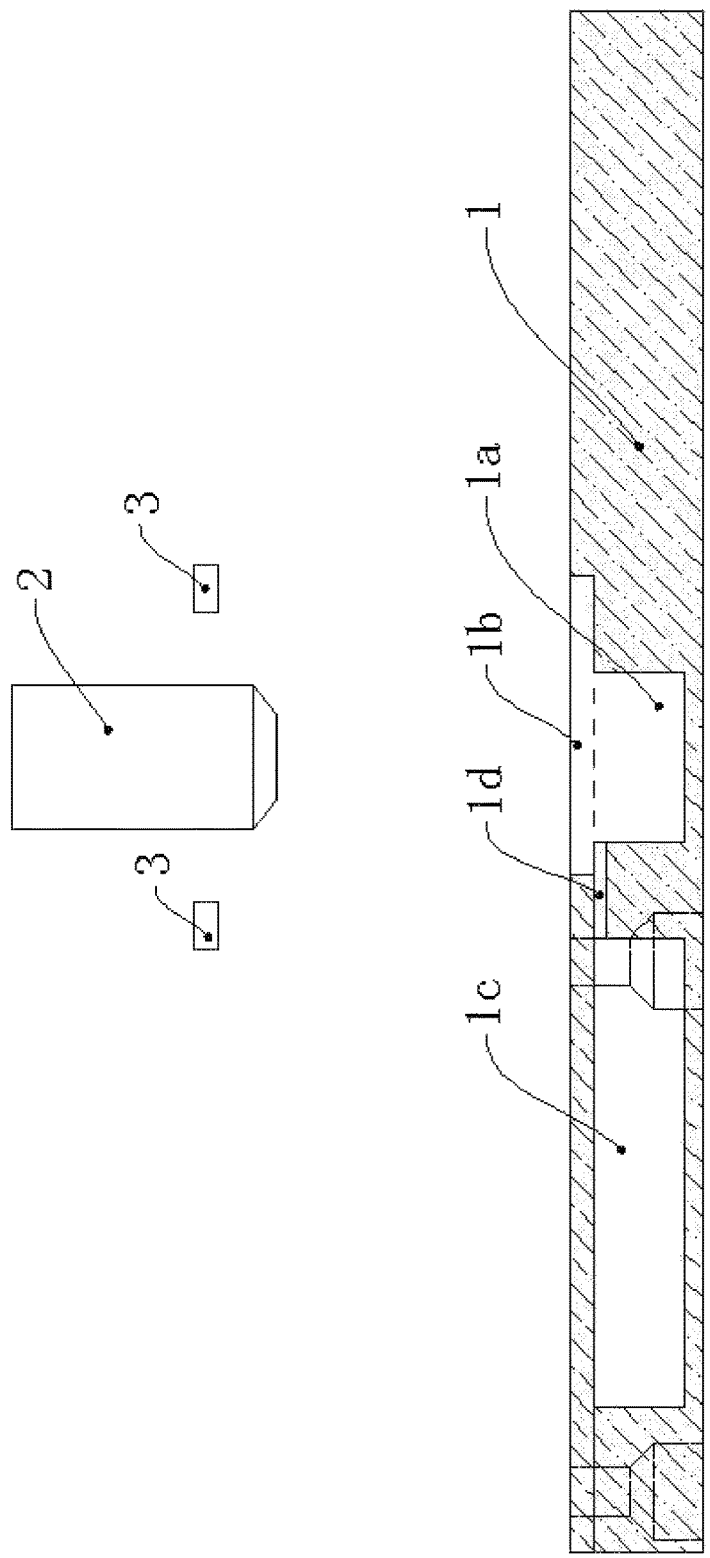
FIG. 2: structural image of the testing sample system in this invention.
Figure 3:
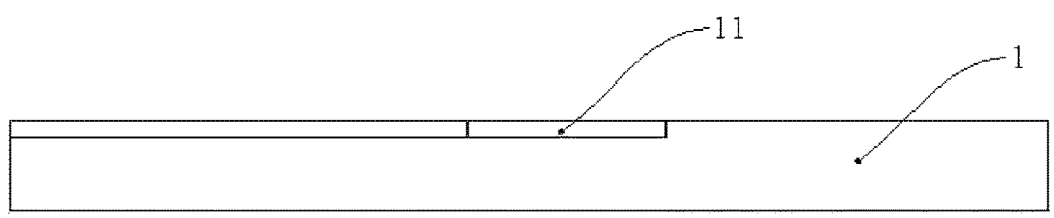
FIG. 3: structural image of reagent card 1 in FIG. 2.
Figure 4:
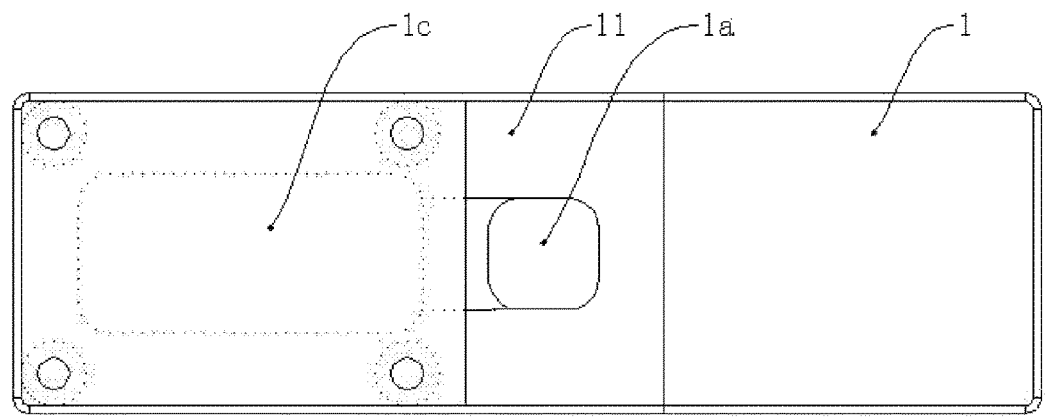
FIG. 4: upward view of FIG. 3.
Figure 5:
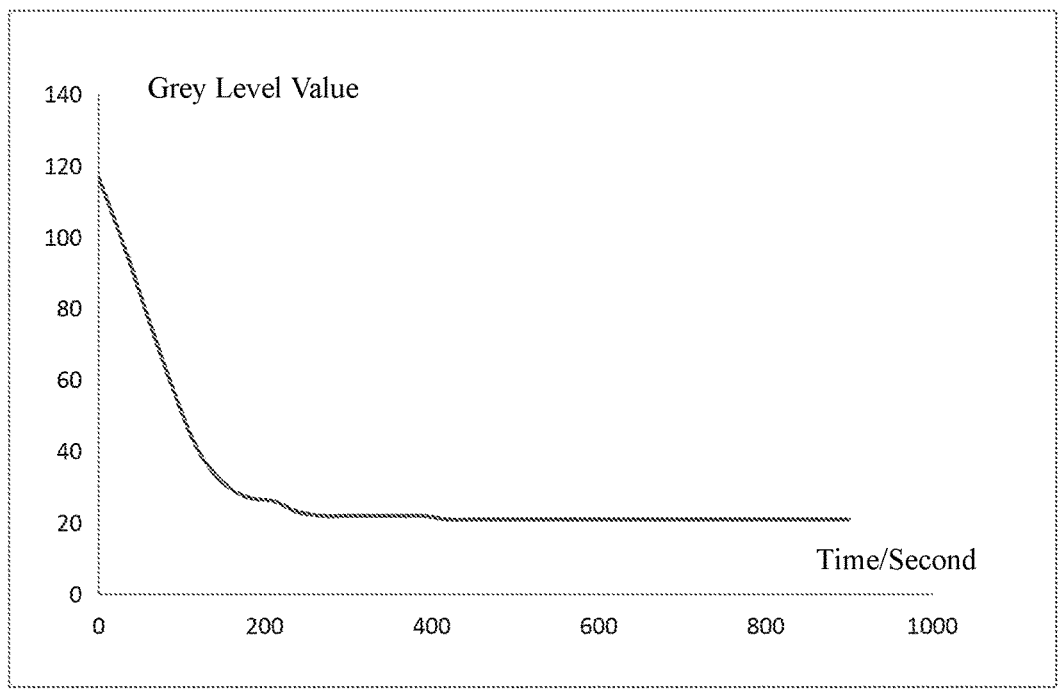
FIG. 5: the grey level value versus time graph obtained by experimental sample 1's data.
Figure 6:
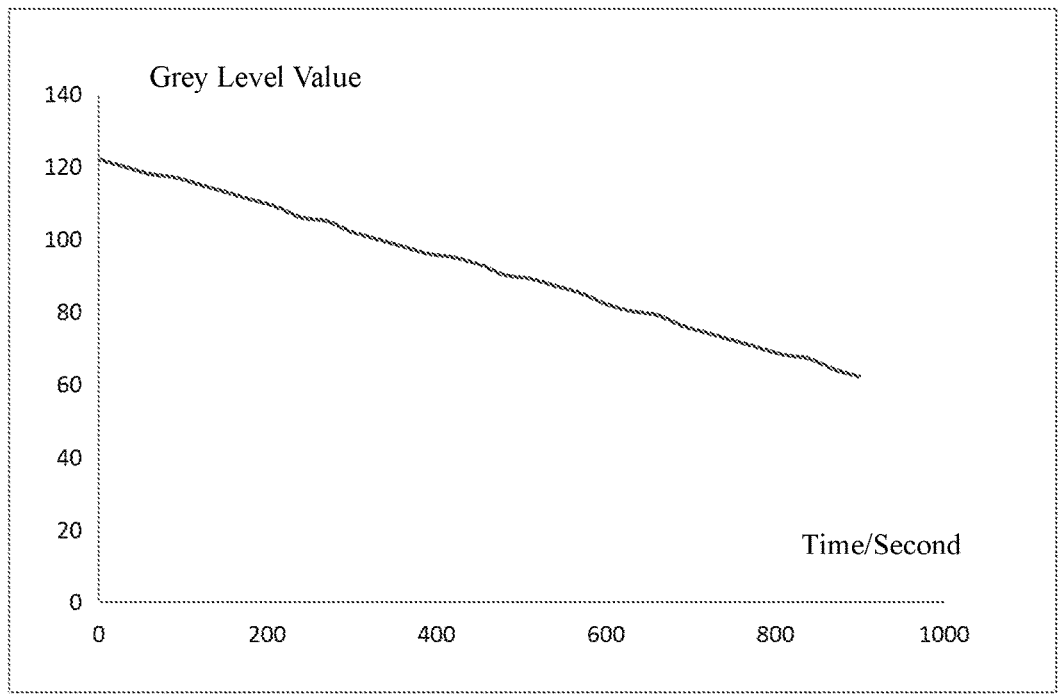
FIG. 6: the grey level versus time graph obtained by experimental sample 2's data.
Figure 7:
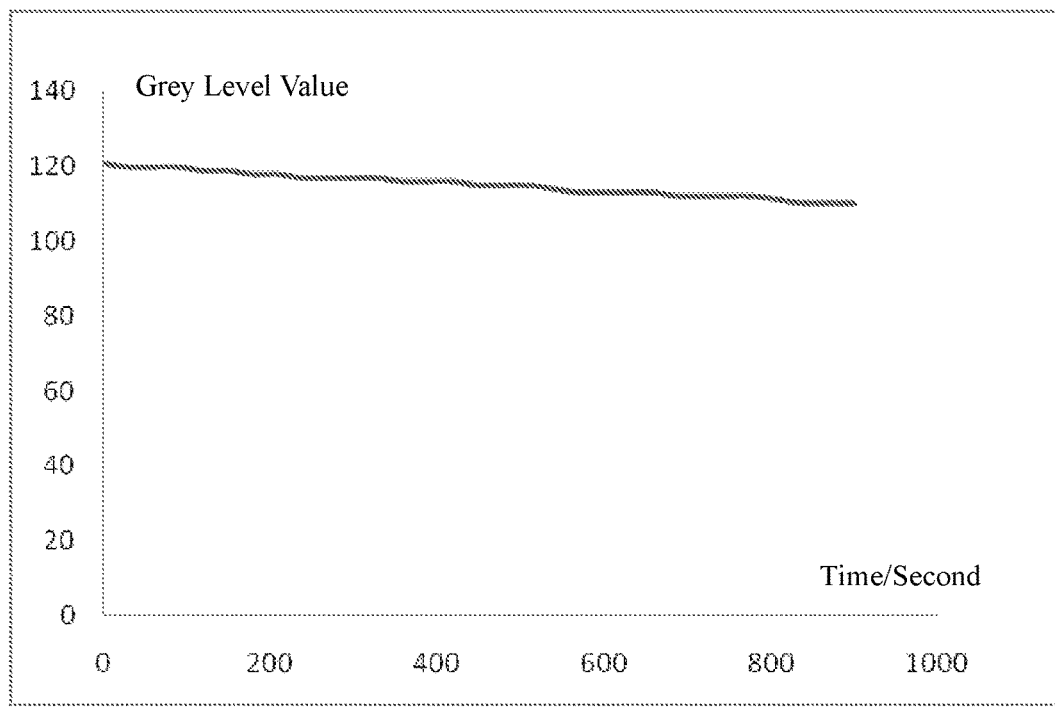
FIG. 7: the grey level versus time graph obtained by experimental sample 3's data.

According to FIGS. 2, 3 and 4, the testing sample system includes testing card 1 and light source 3 above the testing card 1.

The testing card 1 is rectangular shaped, this testing card 1 is made of black plastic material; the testing pool's cover groove 1b is placed on top in the middle of the testing card 1; the sample pool 1a is placed on the bottom of the testing sample cover groove 1b; the sample pool 1a is hold like; surplus sample groove 1c is placed on one side of the testing pool's cover groove 1b on the testing card 1. The surplus sample groove 1c is connected to sample pool 1a by surplus flow groove 1d; one side of the surplus flow groove 1d is connected to hatch on the of the sample pool 1a; other side of the testing cover's groove 1b, the testing card 1 is control area; the testing cover's groove 1b would have placement of transparent cover 11.

The height of the sample pool 1a is 2-5 mm to maintain the same height as semen sample in the sample pool; after sperm sample is added to sample pool, adding the semen sample to fill up the sample pool 1a; then, close the transparent cover 11; relatively isolate the semen sample in the sample pool 1a; avoid some of the effects from out side on the semen liquefaction; surplus semen sample would follow through flow groove into surplus sample groove 1c without outside pollution; after closing the transparent cover 11; the semen sample is even with the height of sample pool 1a; semen sample maintains the same height in the sample pool 1a; to compare different semen samples' liquefaction abilities.

The image collector 2 is placed on top and in the middle of the sample pool 1a; the image collector 2 is image camera or video camera, it also could be other image collector; after adding the semen sample, the image collector 2 is collecting images from sample pool 1a; as the semen sample liquidizes, the transparency of the semen sample increases and blackness from the bottom of sample pool 1a increases; image collector 2 records the change in depth of color of the sample pool 1a in real time and sends the images information to cellphone; the cellphone sends the compressed images information to long distant computer via WIFI of mobile network; long distant computer finishes the images data analysis and grey level color value calculation to obtain testing results and reply back to cellphone's APP at live scene; As the alternative method of connection, the image collector could directly connect to processor; after the processor obtains the results, is directly presents the results to user; but, the device has a high cost which is not suitable for families; thus, utilizing cellphone as connection is more acceptable by family users.

If the natural light source is unstable, the light source 3 could be artificial light source, and the LED light source would be the best; the semen liquefaction ability's testing sample could be placed in the dark box at this time; surrounding the image collector 2 with the light source 3 to set up.

When the natural light source is stable, the light source 3 could utilize natural light source.

TWO. To further explain this invention with combination of experimental samples and figures in the followings:

Picking random semen samples from three people; utilizing the method of testing the quantification of semen liquefaction ability; each semen sample is under same conditions; mark the semen sample added into the sample pool as time 0; all three semen samples are collected from leaving the penis to time 0 without exceeding 2 minutes; starting from time 0, the semen samples' images are collected with the time gap of 30 seconds; stopping the image collection after 10 minutes; obtaining image analysis of each sample; point a stable area as calculating area for each image analysis; choosing 100 evenly distributed pixel points within the calculation area; utilizing RBG color system and 8-digit image to calcite the grey level of the calculating area; the standard pure white grey level is 225.

The actual estimated total grey level value in the appointed calculating area is calculated by using formula 1:

$$\text{Grey Level Value} = \sum_{i=1}^{n} x_i \quad \text{Formula 1}$$

The actual estimated average grey level value of assigned area is calculated by using formula 2.

$$\text{Grey Level Value} = \sum_{i=1}^{n} x_i/n \quad \text{Formula 2}$$

The semen sample's entire grey level value of assigned area is calculated by using formula 3.

$$\text{Grey Level Value} = \sum_{i=1}^{n} (255 - x_i) \quad \text{Formula 3}$$

The semen sample's entire average value of assigned area is calculated by using formula 4.

$$\text{Grey Level Value} = \sum_{i=1}^{n} (255 - x_i)/n \quad \text{Formula 4}$$

n the calculation, n is number of appointed calculating areas' pixel spot; n=100; xi is actual estimated grey level in the pointed calculating areas' each digital pixel spot; estimating the actual grey level of each pixel point is known by technicians within the field; thus, there no need to explain it in this content.

To obtain 3 semen samples by calculation at different times $$\sum_{i=1}^{n} x_i,$$

as shown in table 1.

Thus, 3 semen samples at different times;

The actual estimated total grey value in the appointed calculating $$area = \sum_{i=1}^{n} x_i;$$

The actual estimated average grey value in the appointed calculating $$area = \sum_{i=1}^{n} x_i / 100;$$

The actual relatively total grey value in the appointed calculating $$area = 25500 - \sum_{i=1}^{n} x_i;$$

The actual relatively average grey value in the appointed calculating $$area = \left(25500 - \sum_{i=1}^{n} x_i\right) / 100 = 255 - \sum_{i=1}^{n} x_i / 100.$$

TABLE 1

| sperm samples at different times: | | | |
|---|---|---|---|
| Time/Second | Sample 1 | Sample 2 | Sample 3 |
| 0 | 11745 | 12234 | 12097 |
| 30 | 9842 | 12035 | 12002 |
| 60 | 7696 | 11812 | 11979 |
| 90 | 5674 | 11657 | 11958 |
| 120 | 4017 | 11482 | 11913 |
| 150 | 3130 | 11297 | 11872 |
| 180 | 2724 | 11064 | 11834 |
| 210 | 2583 | 10880 | 11762 |
| 240 | 2332 | 10637 | 11740 |
| 270 | 2235 | 10473 | 11716 |
| 300 | 2196 | 10249 | 11690 |
| 330 | 2177 | 10032 | 11676 |
| 360 | 2165 | 9805 | 11634 |
| 390 | 2153 | 9614 | 11616 |
| 420 | 2149 | 9471 | 11575 |
| 450 | 2147 | 9255 | 11539 |
| 480 | 2147 | 9016 | 11509 |
| 510 | 2147 | 8854 | 11462 |

TABLE 1-continued

| sperm samples at different times: | | | |
|---|---|---|---|
| Time/Second | Sample 1 | Sample 2 | Sample 3 |
| 540 | 2147 | 8661 | 11377 |
| 570 | 2147 | 8479 | 11320 |
| 600 | 2146 | 8233 | 11290 |
| 630 | 2146 | 8045 | 11278 |
| 660 | 2146 | 7891 | 11265 |
| 690 | 2146 | 7617 | 11246 |
| 720 | 2146 | 7439 | 11237 |
| 750 | 2146 | 7236 | 11192 |
| 780 | 2146 | 7070 | 11156 |
| 810 | 2146 | 6821 | 11113 |
| 840 | 2145 | 6684 | 11053 |
| 870 | 2145 | 6425 | 11025 |
| 900 | 2145 | 6208 | 11013 |

According to data from table 1, utilizing formula 1, 2, 3 and 4 to calculate grey level value in order to obtain grey level value versus time graph.

For example, utilizing formula 2 to calculate grey level to draw the grey level value versus time graph from sample 1, 2 and 3; as shown in image 5, 6 and 7.

According to image 5, grey level value of sample 1 decreases as time increases; the grey level value has an obvious decrease within 200 seconds; change ratio of the graph is strong; this phenomenon indicates that semen liquidizes at highest rate within 200 seconds; the change ration of the graph is weaker after first 200 seconds; this phenomenon indicates that the semen liquidizes at lower rate; thus, sample 1 has strong semen liquefaction ability.

According to image 6, grey level value of sample 2 decreases as time increases; the grey level values weaker decrease within 200 seconds comparing to sample 1; change ration of the graph is also weaker than sample 1; until 900 seconds, change ration of the graph is still not obvious; the phenomenon indicates that the semen of sample 2 has not liquidized completely; thus, sample 2 has weak semen liquefaction ability.

According to image 7, grey level value of sample 3 does not decrease as the time increases; change ration of the graph is almost none; thus sample 3 does not have sperm liquefaction ability.

According to image 5, 6 and 7, through quantificational analysis, the semen liquefaction ability could be directly represented; the semen liquefaction speed within a particular time could be precisely obtained by calculating change ratio of grey level within a particular time; the semen liquefaction speed at a particular time could be precisely obtained by calculating change ratio of grey level (curve slope) at a particular time; thus, the semen liquefaction ability could be efficiently, subjectively and standardly estimated in order to eliminate human errors in the testing analysis.

Figure 8:
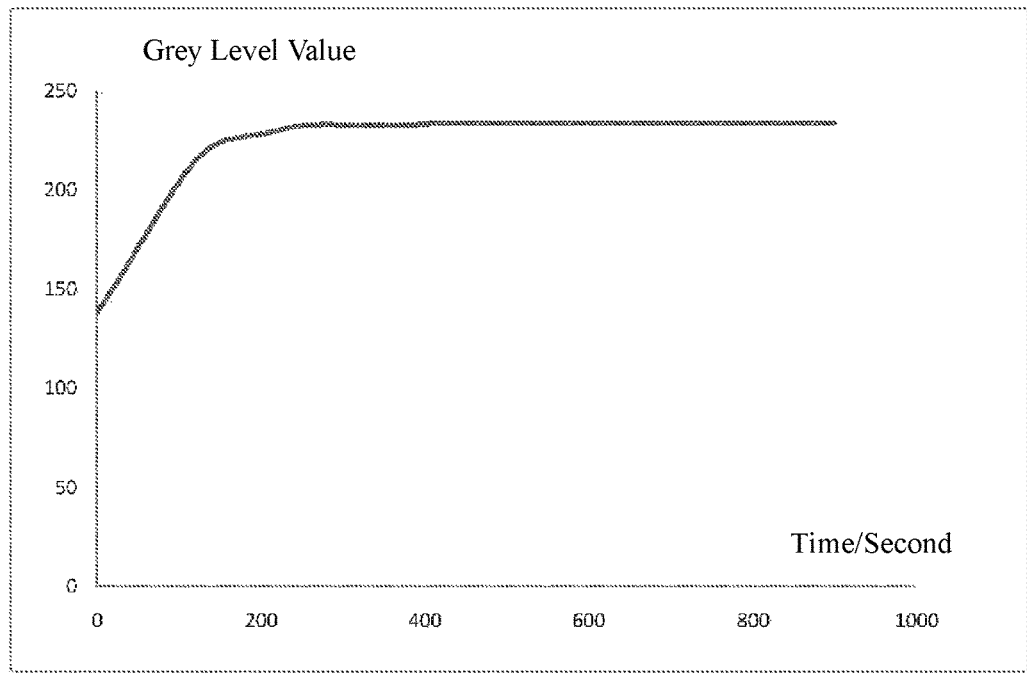
FIG. 8: the grey level versus time graph obtained by experimental sample 1's data using formula 4.
Figure 9:
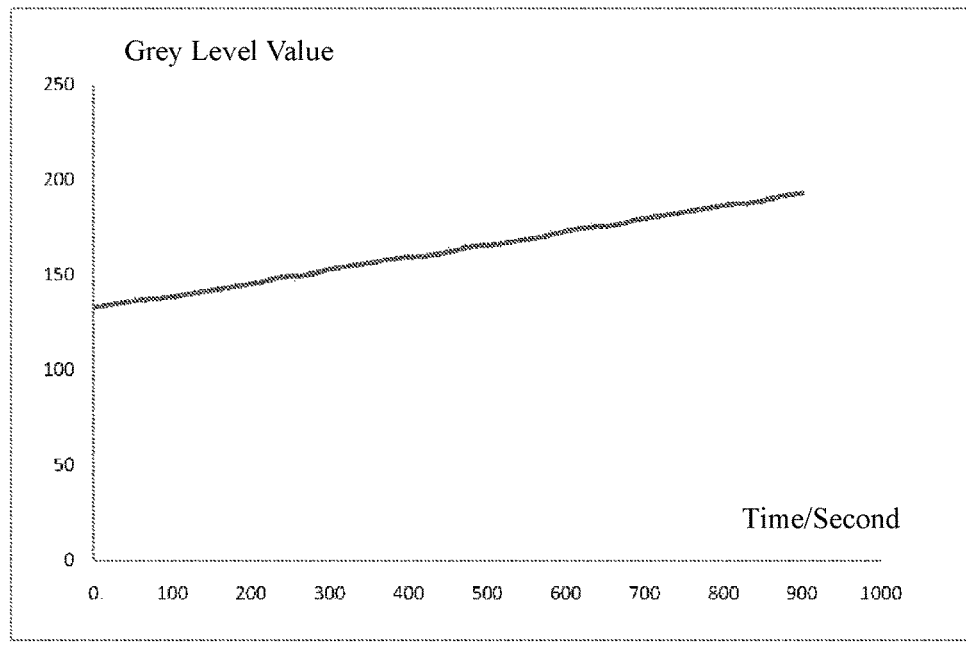
FIG. 9: the grey level versus time graph obtained by experimental sample 2's data using formula 4.
Figure 10:
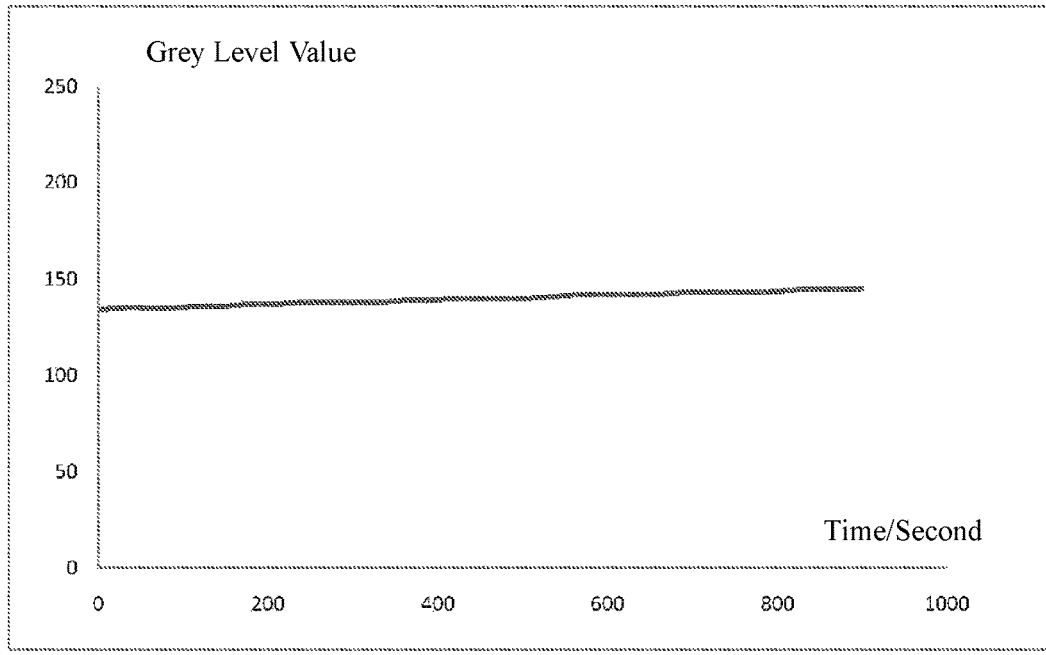
FIG. 10: the grey level versus time graph obtained by experimental sample 3's data using formula 4.

By utilizing formula 4 to calculate grey level values to draw the grey level value versus time graphs of sample 1, 2 and 3, as indicated by FIGS. 8, 9 and 10.

By analyzing FIGS. 8, 9 and 10, estimation would be the same as discussed above.

Lastly, the description in the above is only preferred selection of examples of this invention. By being under the inspiration of this invention and obeying the purpose and rights of this invention, the technician within the field could present this invention in other similar ways; other presentations would be under the protection of this invention.

The invention claimed is:

1. A quantificational testing method of semen liquefaction ability, comprising:

Step 1: sample preparation by adding a semen sample to testing sample system; installing a black sample pool inside the sample's system; adding semen sample to the black sample pool;

Step 2: image collection beginning from adding semen sample to the black sample pool, collecting the semen sample images of the black sample pool by following the time order to receive analyzing images;

Step 3: sample quantification analysis by calculating each image's gray level value to gain gray value versus time graph; wherein a ratio difference of the gray level value to the gain gray value of the graph represents a change of color on the image within the timeline;

Step 4: graph analysis wherein semen liquefaction ability is related to image's change of color; the graph also represents sperm liquefaction ability; the semen liquefaction ability analysis is gained by obtaining gray level value change over time; wherein more change of gray level value over time represents stronger semen liquefaction ability, less change of gray level value over time represents weaker semen liquefaction ability.

2. The method of claim 1, wherein one of the quantification testing method for semen liquefaction ability, its feature is as following: during step 1, the height of black sample pool is 2 to 5 millimeters.

3. The method of claim 2, further comprising: during step 1, the transparent cover plate is placed on top of the black sample pool.

4. The method of claim 1, wherein during step 2, the images are collected at the same height above the black sample pool.

5. The method of claim 4, wherein during step 2, the images are collected at the same time gaps.

6. The method of claim 5, wherein during the step 2, the time gap is between 5 to 60 seconds.

7. The method of claim 1, wherein during step 2, the collection of images is operated under stale lighting conditions.

8. The method of claim 1, wherein during step 3, choosing the same and fixed area of each image to calculated the area's grey level value in order to analyze the grey level value versus time graph.

9. The method of claim 8, wherein during step 3, utilizing RBG color system, eight-digit image calculating grey level value and pure white grey level value at 225, and the actual estimated entire grey level value of assigned area is calculated by using formula 1, wherein $$\text{Grey Level Value} = \sum_{i=1}^{n} x_i; \quad \text{Formula 1}$$

the actual estimated average grey level value of assigned area is calculated by using formula 2, wherein $$\text{Grey Level Value} = \sum_{i=1}^{n} x_i/n; \quad \text{Formula 2}$$

the semen sample's entire grey level value of assigned area is calculated by using formula 3, wherein $$\text{Grey Level Value} = \sum_{i=1}^{n} (255 - x_i); \quad \text{Formula 3}$$

the semen sample's entire average value of assigned area is calculated by using formula 4, wherein $$\text{Grey Level Value} = \sum_{i=1}^{n} (255 - x_i)/n; \quad \text{Formula 4}$$

and during the calculation, n is a pixel number of an assigned area; and xi is an actual estimated gray level of in the assigned area.

10. The method of claim 1, wherein sample testing system includes a testing card, light source above the testing card; the black sample pool is the place at the bottom of cover groove; the bottom of the black sample pool is black; a transparent cover is place in the testing pool's cover groove; the testing card has a surplus sample containing groove; the surplus sample containing groove and sample pool are connected by a surplus flow groove; one end of the surplus flow groove is connected to the top of the black sample pool; there is stable placement of an image collector on top of the black sample pool; the image collector is able to connect to cellphone by wire or wireless connection; and the cellphone is connected to long distant computer.

* * * * *